United States Patent
Kumlin et al.

(10) Patent No.: US 12,121,828 B2
(45) Date of Patent: Oct. 22, 2024

(54) SYSTEMS AND METHODS OF ISOLATION OF GALLIUM-68

(71) Applicant: Telix ARTMS Inc., Toronto (CA)

(72) Inventors: Joel Oscar Olsson Kumlin, Qualicum Beach (CA); Sogol Borjian Borojeni, Vancouver (CA); Daniel Alexander Childs, Maple Ridge (CA)

(73) Assignee: Telix ARTMS Inc., Ontario (CA)

( * ) Notice: Subject to any disclaimer, the term of this patent is extended or adjusted under 35 U.S.C. 154(b) by 0 days.

(21) Appl. No.: 17/767,039

(22) PCT Filed: Oct. 12, 2020

(86) PCT No.: PCT/IB2020/059581
§ 371 (c)(1),
(2) Date: Apr. 6, 2022

(87) PCT Pub. No.: WO2021/070164
PCT Pub. Date: Apr. 15, 2021

(65) Prior Publication Data
US 2022/0351873 A1    Nov. 3, 2022

Related U.S. Application Data

(60) Provisional application No. 62/914,476, filed on Oct. 12, 2019.

(51) Int. Cl.
*A61K 51/00* (2006.01)
*A61M 36/14* (2006.01)
*B01D 15/18* (2006.01)
*B01D 15/26* (2006.01)
*B01D 15/42* (2006.01)
*G21G 1/10* (2006.01)
*G21G 1/00* (2006.01)

(52) U.S. Cl.
CPC ....... *B01D 15/1871* (2013.01); *B01D 15/265* (2013.01); *B01D 15/426* (2013.01); *G21G 1/10* (2013.01); *G21G 2001/0021* (2013.01)

(58) Field of Classification Search
CPC .............. B01D 15/1871; B01D 15/265; B01D 15/426; G21G 1/10; G21G 2001/0021; B01J 45/00; B01J 47/026; A61K 51/0402; A61K 51/083; A61K 51/088; A61K 51/0497
See application file for complete search history.

(56) References Cited

U.S. PATENT DOCUMENTS

| | | | |
|---|---|---|---|
| 2016/0358683 A1 | 12/2016 | Abrunhosa et al. | |
| 2020/0243210 A1* | 7/2020 | Zeisler | G21G 1/001 |
| 2022/0044835 A1* | 2/2022 | Guerin | A61K 51/083 |

FOREIGN PATENT DOCUMENTS

| | | |
|---|---|---|
| WO | 2015/175972 A2 | 11/2015 |
| WO | 2018/039662 A1 | 3/2018 |
| WO | 2019/023787 A1 | 2/2019 |
| WO | 2020/118426 A1 | 6/2020 |

OTHER PUBLICATIONS

Tieu et al. (Nucl. Med. Biol. 2019, 74-75, 12-18).*
TK200 Resin TRISKEM (Product Sheet).*
Ahmed et al. (Hydrometallurgy 2013, 131-132, 24-28).*
TK200 Resin TRISKEM (Product Sheet) 2016.*
A Kasbollah: "Zirconium-89 for positron emission tomography and hydroxamate resin column for gallium-68 generator", Jul. 1, 2013 (Jul. 1, 2013), XP055671697, Retrieved from the Internet: URL: https://pdfs.semanticscholar.org/0f9d/f9d65c2e6929ead2130f7a91ed8564e3f42a.pdf [retrieved on Feb. 26, 2020].
Nakayama M et al: "Separation of 68Ga from 68Ge using a macroporous organic polymer containing N-methylglucamine groups", Analytica Chimica Acta, Elsevier, Amsterdam, NL, vol. 453, No. 1, Feb. 18, 2002 (Feb. 18, 2002), pp. 135-141, XP086256436, ISSN: 0003-2670, DOI: 10.1016/50003-2670(01)01484-2 [retrieved on Jun. 12, 2016].

* cited by examiner

*Primary Examiner* — Michael G. Hartley
*Assistant Examiner* — Melissa J Perreira
(74) *Attorney, Agent, or Firm* — Thomas| Horstemeyer, LLP

(57) ABSTRACT

A process for the preparation of a carrier-free Ga-68 solution from an irradiated Zn target, systems comprising components used in the process, and compositions comprising Ga-68 prepared by the process. Purification of Ga-68 is carried out by feeding an irradiation target solution comprising Zn-68, Ga-68 and solid target assembly metals into a system comprising three chromatography columns in succession.

21 Claims, 6 Drawing Sheets

Back of Irradiated Target

Dissolved Target

Irradiated Target

SYSTEMS AND METHODS OF ISOLATION OF GALLIUM-68

CROSS-REFERENCE TO RELATED APPLICATIONS

This Application is the 35 U.S.C. § 371 national stage application of PCT Application No. PCT/IB2020/059581, filed Oct. 12, 2020, where the PCT claims priority to, and the benefit of U.S. Provisional Application No. 62/914,476, filed on Oct. 12, 2019, both of which are herein incorporated by reference in their entireties.

BACKGROUND

Positron emission tomography (PET) is an imaging method that uses positron emitting radiotracers to track the biochemical, molecular, and/or pathophysiological processes in humans and animals. In PET systems, positron-emitting isotopes serve as beacons for identifying the exact location of diseases and pathological processes under study without surgical exploration of the human body. With these non-invasive imaging methods, the diagnosis of diseases may be more comfortable for patients, as opposed to the more traditional and invasive approaches, such as exploratory surgeries.

One such exemplary radiopharmaceutical agent group includes gallium-68 (Ga-68). Gallium-68 (Ga-68) is a positron emitting radioactive isotope of gallium that is desirable for medical use. Ga-68 possesses several desirable properties for medical use, including a short half-life (t½: 68 min) and a high branching ratio for positron emission (β+%: 89%). Ga-68 tracers may be used for brain, heart, bone, lung or tumor imaging. Specifically, Ga-68 is useful for the production of radiolabeled compounds used as tracer molecules in positron emission tomography (PET) imaging techniques. It forms stable complexes with chelating agents, for example DOTA (1,4,7,10-tetraazacyclododecane-1,4,7,10-tetraacetic acid), NOTA (1,4,7-triazacyclononane-1,4,7-triacetic acid) and H BED-CC (N,N'-bis-[2-hydroxy-5-(carboxyethyl)benzyl]ethylenediamine-N,N'-diaceticacid).

Conventionally, Ga-68 is produced for PET imaging from 68Ge/Ga-68 generators. Unfortunately, although the current state of art, the use of 68Ge/Ga-68 generators has limitations, despite the ability to deliver Ga-68. For example, the Ga-68 activity produced using 68Ge/Ga-68 generators decreases over time due to the decay of the parent nuclide 68Ge (t½: 271 d). Moreover, potential breakthrough of Ge-68 with eluted gallium is an undesirable possible consequence of making Ga-68 using 68Ge/Ga-68 generators. The ability of 68Ge/Ga-68 generators to scale and be able to deliver the amounts of Ga-68 that are anticipated to be required for medical use is in question, in part, due to limitations on the ability to produce sufficient quantities of 68Ge.

Although cyclotron production of Ga-68 provides a way to meet a large demand for Ga-68 while eliminating the shortcomings associated with production using 68Ge/Ga-68 generators, including the possibility of 68Ge breakthrough during the production process, e.g., as disclosed in International Patent Application PCT/CA2018/000146, there remains a need for efficient and rapid isolation of Ga-68 produced using solid zinc targets irradiated by an accelerated particle beam. In particular, there is a need for isolation of Ga-68 produced using solid zinc targets irradiated by an accelerated particle beam that meets or surpasses all the requirements set forth in European Pharmacopoeia (Ph. Eur.) draft monograph 3109. These needs and other needs are satisfied by the present disclosure.

SUMMARY

In accordance with the purpose(s) of the present disclosure, as embodied and broadly described herein, the disclosure, in one aspect, relates to processes for preparation of a carrier-free Ga-68 solution from a solid target assembly, systems comprising components used in the disclosed processes, and compositions comprising Ga-68 prepared by the disclosed processes.

In various aspects, the disclosed processes for preparation of a carrier-free Ga-68 solution from a solid target assembly, the process comprising: adsorbing an irradiation target solution to a first chromatography column comprising a first chromatographic resin; washing the first chromatography column with a first chromatography wash solution; eluting a first eluate solution from the first chromatography column with a first chromatography column elution solution; adsorbing the first eluate solution to a second chromatography column comprising a second chromatography resin; collecting a second chromatography column flow-through solution from the second chromatography column; adsorbing the second chromatography column flow-through solution to a third chromatography column comprising a third chromatography resin; and eluting the carrier-free Ga-68 solution from the third chromatography column with a third chromatography column elution solution; wherein the irradiation target solution comprises a solution formed by dissolution of at least a portion of an irradiation target portion of a solid target assembly; wherein the irradiation target solution comprises Zn-68, Ga-68, and solid target assembly metals; wherein the solid target assembly comprises a metal disc comprising front and rear surfaces, and the irradiation target portion disposed on the top surface of the disc; wherein the irradiation target portion comprises a mixture of Zn-68 and Ga-68; wherein the first chromatography resin comprises a hydroxamate chromatography resin; wherein the first chromatography column wash solution has a strong acid present at a concentration of greater than about 4.5 M; wherein the first chromatography column elution solution has a strong acid present at a concentration of less than about 3.5 M; wherein the second chromatography resin comprises an alkyl phosphine oxide chromatography resin; wherein the third chromatography resin comprises an alkyl orthophosphoric acid chromatography resin; and wherein the third chromatography column elution solution is optionally comprises a strong acid present at a concentration less than about 0.2 M.

Also disclosed herein are Ga-68 compositions comprising Ga-68 obtained from the carrier-free Ga-68 solution prepared by a disclosed process.

Also disclosed are imaging reagent comprising a disclosed Ga-68 composition, e.g., imaging reagents such as $^{68}$Ga-PSMA-617, $^{68}$Ga-PSMA-11, $^{68}$Ga-DOTATATE, $^{68}$Ga-DOTATOC, $^{68}$Ga-DOTANOC, or combinations thereof.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims. In addition, all optional and preferred features and modifications of the described aspects are usable in all aspects of the disclosure taught herein. Furthermore, the individual features of the dependent claims, as well as all optional and preferred features and modifications of the described aspects are combinable and interchangeable with one another.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 6A shows a 68-Zn target following irradiation. FIG. 6B shows an irradiated 68-Zn target following a disclosed dissolution step. FIG. 6C shows the back of the irradiated target shown in FIG. 6A.

Figure 1:
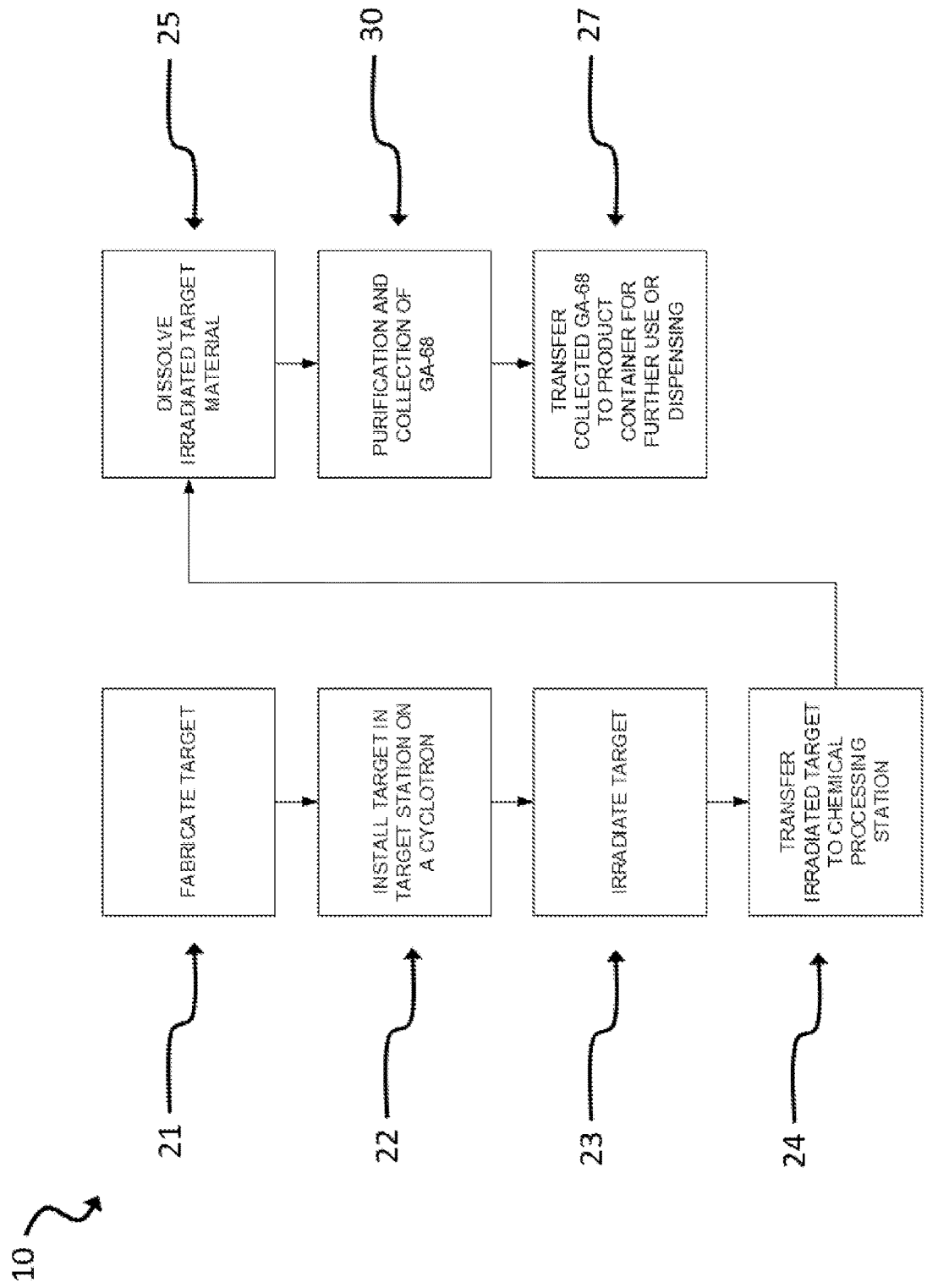
FIG. 1 shows a representative process for production of Ga-68 using solid zinc targets irradiated by an accelerated particle beam.

Additional advantages of the disclosure will be set forth in part in the description which follows, and in part will be obvious from the description, or can be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

DETAILED DESCRIPTION

Many modifications and other aspects disclosed herein will come to mind to one skilled in the art to which the disclosed compositions and methods pertain having the benefit of the teachings presented in the foregoing descriptions and the associated drawings. Therefore, it is to be understood that the disclosures are not to be limited to the specific aspects disclosed and that modifications and other aspects are intended to be included within the scope of the appended claims. The skilled artisan will recognize many variants and adaptations of the aspects described herein. These variants and adaptations are intended to be included in the teachings of this disclosure and to be encompassed by the claims herein.

Although specific terms are employed herein, they are used in a generic and descriptive sense only and not for purposes of limitation.

As will be apparent to those of skill in the art upon reading this disclosure, each of the individual aspects described and illustrated herein has discrete components and features which may be readily separated from or combined with the features of any of the other several aspects without departing from the scope or spirit of the present disclosure.

Any recited method can be carried out in the order of events recited or in any other order that is logically possible. That is, unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present disclosure is not entitled to antedate such publication by virtue of prior disclosure. Further, the dates of publication provided herein can be different from the actual publication dates, which can require independent confirmation.

While aspects of the present disclosure can be described and claimed in a particular statutory class, such as the system statutory class, this is for convenience only and one of skill in the art will understand that each aspect of the present disclosure can be described and claimed in any statutory class.

It is also to be understood that the terminology used herein is for the purpose of describing particular aspects only and is not intended to be limiting. Unless defined otherwise, all technical and scientific terms used herein have the same meaning as commonly understood by one of ordinary skill in the art to which the disclosed compositions and methods belong. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

Prior to describing the various aspects of the present disclosure, the following definitions are provided and should be used unless otherwise indicated. Additional terms may be defined elsewhere in the present disclosure.

REFERENCE NUMBER GLOSSARY

The following is a glossary of reference numbers and the term of reference used with each number. The reference numbers are used herein throughout in the figures and detailed description. It is understood that like numbers have the same meaning when used elsewhere.

| Reference Number Glossary. | |
|---|---|
| Reference Number | Term of Reference |
| 10 | Process for irradiation and purification of Ga-68 |
| 21 | Fabricate target step |
| 22 | Install target step |
| 23 | Irradiate target step |
| 24 | Target transfer step |
| 25 | Dissolution step |

-continued
Reference Number Glossary.

| Reference Number | Term of Reference |
|---|---|
| 40 | Purification step |
| 27 | Collection step |
| 30 | Exemplary disclosed Ga-68 purification process |
| 41 | Column 1 adsorption step |
| 42 | Column 1 wash step |
| 43 | Column 1 elution step |
| 44 | Column 1 eluate collection step |
| 45 | Column 2 adsorption step |
| 46 | Column 2 wash step |
| 46a | Column 2 wash step |
| 46b | Column 2 unbound collection step |
| 47 | Column 3 adsorption step |
| 48 | Column 3 elution step |
| 49 | Column 3 collection step |
| 50 | Exemplary Ga-68 purification system |
| 62 | Input 4-way valve |
| 63 | Column 1 3-way valve |
| 64 | Column 2 3-way valve |
| 65 | Column 3 3-way valve |
| 71 | Column 1 |
| 72 | Column 2 |
| 73 | Column 3 |
| 81 | Column 1 wash solution reservoir |
| 82 | Column 1 elution solution reservoir |
| 83 | Column 3 elution solution reservoir |
| 91 | Input (dissolved irradiation target) |
| 92 | Output (purified Ga-68) |
| 101 | Column 1 wash removal |
| 102 | Column 3 flow-through removal |

Definitions

As used herein, "comprising" is to be interpreted as specifying the presence of the stated features, integers, steps, or components as referred to, but does not preclude the presence or addition of one or more features, integers, steps, or components, or groups thereof. Moreover, each of the terms "by", "comprising," "comprises", "comprised of," "including," "includes," "included," "involving," "involves," "involved," and "such as" are used in their open, non-limiting sense and may be used interchangeably. Further, the term "comprising" is intended to include examples and aspects encompassed by the terms "consisting essentially of" and "consisting of." Similarly, the term "consisting essentially of" is intended to include examples encompassed by the term "consisting of".

As used herein, the term "and/or" includes any and all combinations of one or more of the associated listed items. Expressions such as "at least one of," when preceding a list of elements, modify the entire list of elements and do not modify the individual elements of the list.

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

Reference to "a" chemical compound refers to one or more molecules of the chemical compound rather than being limited to a single molecule of the chemical compound. Furthermore, the one or more molecules may or may not be identical, so long as they fall under the category of the chemical compound. Thus, for example, "a" chemical compound is interpreted to include one or more molecules of the chemical, where the molecules may or may not be identical (e.g., different isotopic ratios, enantiomers, and the like).

As used in the specification and the appended claims, the singular forms "a," "an" and "the" include plural referents unless the context clearly dictates otherwise. Thus, for example, reference to "a chromatography resin," "a radionuclide," or "a strong acid," including, but not limited to, two or more such chromatography resins, radionuclides, or strong acids, and the like.

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

When a range is expressed, a further aspect includes from the one particular value and/or to the other particular value. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used herein, the terms "about," "approximate," "at or about," and "substantially" mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In such cases, it is generally understood, as used herein, that "about" and "at or about" mean the nominal value indicated ±10% variation unless otherwise indicated or inferred. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

As used herein, the terms "gallium-68", "Ga-68", and "68-Ga" can be used interchangeably and refer to the positron-emitting radioactive isotope $^{68}Ga$ (Z=31; N=37; isotopic mass=67.9279801; $t_{1/2}$=67.71 minutes). Ga-68 is desirable for medical use. Ga-68 possesses two desirable properties for medical use, a short half-life (t½: 68 min) and a high branching ratio for positron emission (β+%: 89%). Ga-68 can be in a cyclotron via the 68Zn(p,n)Ga-68 reaction in a solid target.

As used herein, the term "effective amount" refers to an amount that is sufficient to achieve the desired modification of a physical property of the composition or material. For example, an "effective amount" of a strong acid to bind a material to a chromatography resin refers to an amount or concentration that is sufficient to causing quantitative (e.g., >90%) binding of a material in a solution to a chromatography resin.

As used herein, the terms "optional" or "optionally" means that the subsequently described event or circumstance can or cannot occur, and that the description includes instances where said event or circumstance occurs and instances where it does not.

Unless otherwise specified, temperatures referred to herein are based on atmospheric pressure (i.e. one atmosphere).

Processes for Purification of Ga-68 from Irradiated Zn Target

In various aspects, disclosed herein are processes for preparation of a carrier-free Ga-68 solution from a solid target assembly, the process comprising: adsorbing an irradiation target solution to a first chromatography column comprising a first chromatographic resin; washing the first chromatography column with a first chromatography wash solution; eluting a first eluate solution from the first chromatography column with a first chromatography column elution solution; adsorbing the first eluate solution to a second chromatography column comprising a second chromatography resin; collecting a second chromatography column flow-through solution from the second chromatography column; adsorbing the second chromatography column flow-through solution to a third chromatography column comprising a third chromatography resin; and eluting the carrier-free Ga-68 solution from the third chromatography column with a third chromatography column elution solution; wherein the irradiation target solution comprises a solution formed by dissolution of at least a portion of an irradiation target portion of a solid target assembly; wherein the irradiation target solution comprises Zn-68, Ga-68, and solid target assembly metals; wherein the solid target assembly comprises a metal disc comprising front and rear surfaces, and the irradiation target portion disposed on the top surface of the disc; wherein the irradiation target portion comprises a mixture of Zn-68 and Ga-68; wherein the first chromatography resin comprises a hydroxamate chromatography resin; wherein the first chromatography column wash solution has a strong acid present at a concentration of greater than about 4.5 M; wherein the first chromatography column elution solution has a strong acid present at a concentration of less than about 3.5 M; wherein the second chromatography resin comprises an alkyl phosphine oxide chromatography resin; wherein the third chromatography resin comprises an alkyl orthophosphoric acid chromatography resin; and wherein the third chromatography column elution solution is optionally comprises a strong acid present at a concentration less than about 0.2 M.

Ga-68 has a short half-life of 68 minutes. Accordingly, the disclosed processes provide improved decay-corrected separation chemistry that provides optimal processing times while maintaining suitable yields of Ga-68.

Figure 2:
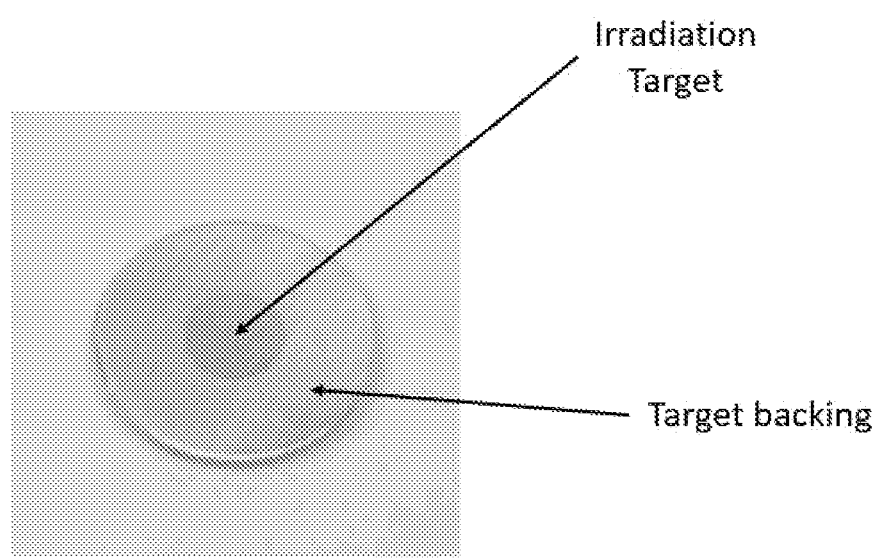
FIG. 2 shows a representative photographic image of an irradiation target with target backing.

In various aspects, the irradiation target solution comprises a solution formed by dissolution of at least a portion of an irradiation target portion of a solid target assembly. A representative solid target assembly is shown in FIG. 2, which comprises an irradiation target and a target backing. The irradiation target, prior to irradiation by a suitable cyclotron particle beam, comprises Zn-68, e.g., the Zn-68 can be present in a wt % amount of about 95 wt % to about 99.9 wt %. Following suitable irradiation, the irradiation target comprises Ga-68, representing conversion of at least a portion of Zn-68 to Ga-68. Suitable solid target assembly apparatus and methods of irradiation to convert at least a portion of the Zn-68 to Ga-68 are described in International Patent Appl. No. PCT/CA2017/000146, which is incorporated herein in its entirety.

The irradiation target solution can be formed by dissolution of a solid target assembly, in particular, dissolution of the irradiation target following irradiation, i.e., a material enriched in Ga-68 by conversion from Zn-68 using cyclotron particle beam irradiation as described in International Patent Appl. No. PCT/CA2017/000146. Dissolution of the solid target assembly can be principally the dissolution of the irradiation target following irradiation, but can include partial or complete dissolution of the target backing. Dissolution can be effected by contacting the solid target assembly with a suitable acid, e.g., hydrochloric, nitric, and/or acetic acid. In some aspects, dissolution using acetic acid can be expedited by adding a small quantity of an oxidizing agent, such as hydrogen peroxide, and/or by applying heat. The resulting acetate solution may be evaporated and taken up in hydrochloric acid for subsequent standard ion exchange separation. In other aspects, the dissolution method can use hydrochloric acid or nitric acid. In some instances, it may be advantageous to use nitric acid which can selectively dissolve zinc while the oxidizing properties of nitric acid increase the thickness of the natural oxide layer on metallic aluminum, thus protecting it from attack by the acid. The dissolution of zinc proceeds rapidly, and a wide range of concentrations may be used. In further aspects, it may be advantageous to use hydrochloric acid for the dissolution method. The acid solutions for dissolution are traditionally strongly acidic, often hydrochloric acid (HCl), but nitric acid ($HNO_3$) and acetic acid ($CH_3COOH$) can also be used. Typically, the dissolved target solution can contain >5N HCl. In some instances, irradiation target solution used in the disclosed processes is a liquid target having a concentration of acid that can <1 N HCl or <1 N $HNO_3$.

For example, the solid target assembly can be contacted with a target assembly dissolution solution comprising a suitable acid, e.g., a strong acid such as hydrochloric acid, at a concentration of from about 4.5 M to about 12.2 M, about 8 M to about 12.2 M, about 12 to about 12.2 M, any concentration sub-range within any of the foregoing ranges, or a concentration or set of concentration values within the foregoing ranges. The pH of the solution contacting the solid target assembly, comprising a suitable acid, has a pH of from about 0.7 to about 4, about 1 to about 2, about 1.5 to 2, any pH sub-range within any of the foregoing ranges, or any pH or set of pH values within the foregoing ranges. The solid target assembly is contacted with the target assembly dissolution solution for a suitable period of time at a suitable temperature, e.g., from about 30 seconds to about 30 minutes at a temperature of from about 10° C. to about 100° C., thereby forming the irradiation target solution.

The irradiation target solution prepared from a typical solid or liquid cyclotron target to produce radioactive gallium isotopes can consist of significant quantities of zinc, iron and sometimes aluminum and other metals. For example, when processing from solid targets as described above using a dissolution method as described herein, a typical irradiation target solution will contain 100-400 mg Zn, μg quantities of Fe and sometimes up to 20 mg aluminum.

In various aspects, the irradiation target solution can comprise from about 1 mg to about 5000 mg Zn-68 in a volume of from about 0.5 mL to about 20 mL. In a further aspect, the irradiation target solution can comprise from about 50 mg to about 500 mg Zn-68 in a volume of from about 1 mL to about 5 mL. In a still further aspect, the irradiation target solution can comprise from about 250 mg to about 350 mg Zn-68 in a volume of from about 2 mL to about 3 mL.

In the process disclosed herein, the adsorbing the irradiation target solution to a first chromatography column comprising a first chromatographic resin can be carried out a flow rate of from about 0.1 mL/min to about 30 mL/min, about 1 mL/min to about 6 mL/min, about 2 mL/min to about 4 mL/min, or a flow rate sub-range within any of the foregoing ranges, or a flow rate value or set of flow rate values within any of the foregoing ranges.

The first chromatography resin can be a suitable chromatography resin comprising hydroxamic acid and/or hydroxamic acid functionalities, i.e., a hydroxamate chromatography resin. The hydroxamate chromatography resin can have a particle size of from about 10 μm to about 300 μm, about 50 μm to about 150 μm, about 50 μm to about 100 μm, or a particle size range that is a sub-range within any of the foregoing ranges, or a particle size value or set of particle size values within any of the foregoing ranges. The amount of the first chromatography resin used for the irradiation target solutions described above can be from about 20 mg to about 10 g, about 100 mg to about 500 mg, about 200 mg to about 300 mg, or a resin amount range that is a sub-range within any of the foregoing ranges, or a resin amount value or set of resin amount values within any of the foregoing ranges.

Under the conditions that adsorbation step of the irradiation target solution onto the first chromatography column is carried out as described above, the Ga-68 will bind to the hydroxamate functional groups of the first chromatography resin, whereas ions such as zinc and aluminum have low binding-affinity to the first chromatography resin and are believed to flow through the column.

Exemplary methods for the preparation of suitable hydroxamate chromatography resins are described in the dissertation entitled "Chelating ion exchange with macroreticular hydroxamic acid resins" (Richard James Philips, Iowa State University, 1980). Suitable resins are also commercially available, e.g., ZR Resin and related resins available from Triskem International (Bruz, France).

Following adsorbation of the irradiation target solution to the first chromatography column, it can be washed with the first chromatography wash solution. The first chromatography wash solution can be substantially similar to the dissolution solution used in the dissolution step. The first chromatography wash solution comprises a suitable acid, e.g., a strong acid such as hydrochloric acid, at a concentration of from about 4.5 M to about 12.2 M, about 8 M to about 12.2 M, about 12 M to about 12.2 M, any concentration sub-range within any of the foregoing ranges, or a concentration or set of concentration values within the foregoing ranges. The pH of the first chromatography wash solution can have a pH of from about 0.7 to about 4, about 1 to about 2, about 1.5 to 2, any pH sub-range within any of the foregoing ranges, or any pH or set of pH values within the foregoing ranges. The first chromatography wash solution can be provided at a flow rate of from about 0.1 mL/min to about 30 mL/min, about 1 mL/min to about 6 mL/min, about 2 mL/min to about 4 mL/min, or a flow rate sub-range within any of the foregoing ranges, or a flow rate value or set of flow rate values within any of the foregoing ranges. The volume of the first chromatography wash solution can be from about 4 mL to about 50 mL, about 8 mL to about 20 mL, about 12 mL to about 18 mL; or a volume sub-range within any of the foregoing ranges; or a volume value or set of volume values within any of the foregoing ranges. The wash step described above is carried out to further rinse from the column any zinc or aluminum ions that may be present in the first chromatography resin.

Following the completion of washing the first chromatography column with the first chromatography wash solution, Ga-68 is eluted from the first chromatography column using the first chromatography elution solution. The first chromatography elution solution comprises a suitable acid, e.g., a strong acid such as hydrochloric acid, at a concentration of from about 0.2 N to about 3.5 N, about 0.5 N to about 3 N, about 1 N to about 2 N; or any concentration sub-range within any of the foregoing ranges; or a concentration or set of concentration values within the foregoing ranges. The volume of the first chromatography elution solution can be from about 2 mL to about 20 mL, about 5 mL to about 10 mL, about 6 mL to about 8 mL; or a volume sub-range within any of the foregoing ranges; or a volume value or set of volume values within any of the foregoing ranges. The first chromatography elution solution can be provided to the first chromatography column at a flow rate of from about 0.1 mL/min to about 10 mL/min, about 1 mL/min to about 4 mL/min, about 1.5 mL/min to about 2.5 mL/min, or a flow rate sub-range within any of the foregoing ranges, or a flow rate value or set of flow rate values within any of the foregoing ranges.

The eluate from the first chromatography column, i.e., the first eluate solution, can be provided directly to the second chromatography column without further processing. That is, the first eluate solution can be directly loaded onto the second chromatography column. Under the disclosed conditions, it is believed that the Ga-68 does not generally bind to the second chromatography resin under the conditions described herein, whereas certain contaminants such as iron ions will bind to the second chromatography resin under these conditions.

The second chromatography resin can be a suitable chromatography resin comprising dialkylorthophosphoric acid functionalities, e.g., di(2-ethylhexyl)orthophosphoric acid (HDEHP) functionalities. The second chromatography resin can have a particle size of from about 10 μm to about 300 μm, about 20 μm to about 150 μm, about 50 μm to about 150 μm, or a particle size range that is a sub-range within any of the foregoing ranges, or a particle size value or set of particle size values within any of the foregoing ranges. The amount of the second chromatography resin used for the irradiation target solutions described above can be from about 100 mg to about 1 g, about 300 mg to about 700 mg, about 450 mg to about 550 mg, or a resin amount range that is a sub-range within any of the foregoing ranges, or a resin amount value or set of resin amount values within any of the foregoing ranges. Suitable resins are also commercially available, e.g., LN Resin, e.g., LN, LN2, or LN3, and related resins available from Triskem International (Bruz, France).

Since the Ga-68 does not bind to the second chromatography resin, it will flow through the second chromatography column and the flow through volume can be provided directly to the third chromatography column comprising the third chromatography resin. The Ga-68 is believed to generally bind to the third chromatography resin under the conditions described herein, whereas other contaminants that may be present do not bind to the third chromatography resin under these conditions. The third chromatography resin is a suitable resin such as a resin comprising trialkylphosphine oxide functionalities, e.g., trioctylphosphine oxide (TOPO) functionalities. The third chromatography resin can have a particle size of from about 10 μm to about 300 μm, about 20 μm to about 150 μm, about 50 μm to about 100 μm, or a particle size range that is a sub-range within any of the foregoing ranges, or a particle size value or set of particle size values within any of the foregoing ranges. The amount of the third chromatography resin used for the irradiation target solutions described above can be from about 20 mg to about 10 g, about 100 mg to about 300 mg, about 150 mg to about 250 mg, or a resin amount range that is a sub-range within any of the foregoing ranges, or a resin amount value or set of resin amount values within any of the foregoing ranges. Suitable resins are also commercially available, e.g., TK200 Resin and related resins available from Triskem International (Bruz, France).

Following adsorbing the second chromatography column flow through volume to the third chromatography column, the desired Ga-68 can be eluted with a suitable third chromatography column elution solution comprising essentially water or a low concentration of a suitable acid, e.g., a strong acid such as hydrochloric acid. If the third chromatography column elution solution comprises a suitable acid, e.g., a strong acid such as hydrochloric acid, then the suitable acid can be present at a concentration of from about 0.001 N to about 0.2 N, about 0.001 N to about 0.1 N, about 0.01 N to about 0.05 N; or any concentration sub-range within any of the foregoing ranges; or a concentration or set of concentration values within the foregoing ranges. The volume of the third chromatography elution solution can be from about 1 mL to about 100 mL, about 1 mL to about 20 mL, about 2 mL to about 5 mL; or a volume sub-range within any of the foregoing ranges; or a volume value or set of volume values within any of the foregoing ranges. The third chromatography elution solution can be provided to the third chromatography column at a flow rate of from about 0.1 mL/min to about 30 mL/min, about 1 mL/min to about 6 mL/min, about 2 mL/min to about 4 mL/min, or a flow rate sub-range within any of the foregoing ranges, or a flow rate value or set of flow rate values within any of the foregoing ranges.

Referring now to FIG. 1, a representative process for irradiation and purification of Ga-68 10 for production of Ga-68 using solid zinc targets irradiated by an accelerated particle beam. That is, the process shown in FIG. 1 comprises the disclosed isolation and purification process within the overall process scheme of fabricating a suitable irradiation target and irradiating said target.

The process for irradiation and purification of Ga-68 10 can comprise the step fabricate target 21, i.e., fabrication of a suitable target comprising Zn-68. A suitable method of fabricating a suitable target comprising Zn-68 is described in PCT/CA2018/000146, which is incorporated herein in its entirety. The zinc material of the target comprises a composition comprising Zn-68.

In a further aspect, the zinc material mostly contains zinc Zn-68 (at least 90%), a stable (non-radioactive) isotope of zinc, and also has traces of other zinc isotopes, such as Zn-64, Zn-66, Zn-67, and/or Zn-70 and other elements, such as Al, As, Ca, Cd, Co, Cr, Cu, Fe, K, Mg, Mn, Na, Pb, Si, and/or Sn. The zinc material can be placed on a target backing material made of chemically inert metals, such as the noble metals or the refractory metals, or any other material with a high thermal conductivity that is suitable for mechanical or other modification and bonds easily to zinc, such as silver, copper or aluminum. The backing material is of sufficient robustness to dissipate an exemplary proton beam current of at least approximately 10 μA and energy of approximately 15 MeV on a beam spot of approximately 10 mm diameter.

The fabricate target step 21 can be followed by an install target step 22, i.e., installing (or transferring) the target to an irradiation apparatus that has the target in a beam path of a suitable cyclotron. The install target step 22 is followed by an irradiate target step 23, i.e., irradiation of the zinc target described herein above. The irradiate target step 23 comprises irradiating the target for a predetermined period of time with a suitable proton beam, e.g., irradiation with a proton beam having a current of up to 100 μA, beam energy of no more than 12.7 MeV, and a beam spot of approximately 10 mm diameter. In a still further aspect, the apparatus 10 is irradiated for at least 5 minutes and no more than approximately hours. The irradiate target step 23 of the zinc target also produces other isotopes such as Ga-64, Ga-66, Ga-67, and Ga-70. These other radioisotopes decay over time (i.e. 2 minutes-3 days). After irradiation, the Ga-68 that forms in irradiated zinc target material can be separated from the irradiated target using the disclosed processes.

The irradiated target produced in the irradiate target step 23 is then transferred from the irradiation station to a processing station comprising the disclosed systems of the present disclosure. Once in the process station, the target is subjected to a dissolution step wherein the irradiated zinc material is dissolved in a dissolution step 24. The solution produced in the dissolution step 24 can be transferred to disclosed purification system 50 for carrying out the purification step 40. The outlet of the disclosed purification system 50 allows collection of the purified Ga-68 in the collection step 27. In some aspects, the disclosed purification step 40 can further comprise the dissolution step 24 and/or the collection step 27. Accordingly the disclosed purification system 50 can further comprise components and/or devices for carrying out the dissolution step 25 and/or the collection step 27. As described herein below, the disclosed purification system 40 can also further comprise control elements comprising computer-controlled or actuated valves and pumps.

Figure 3:
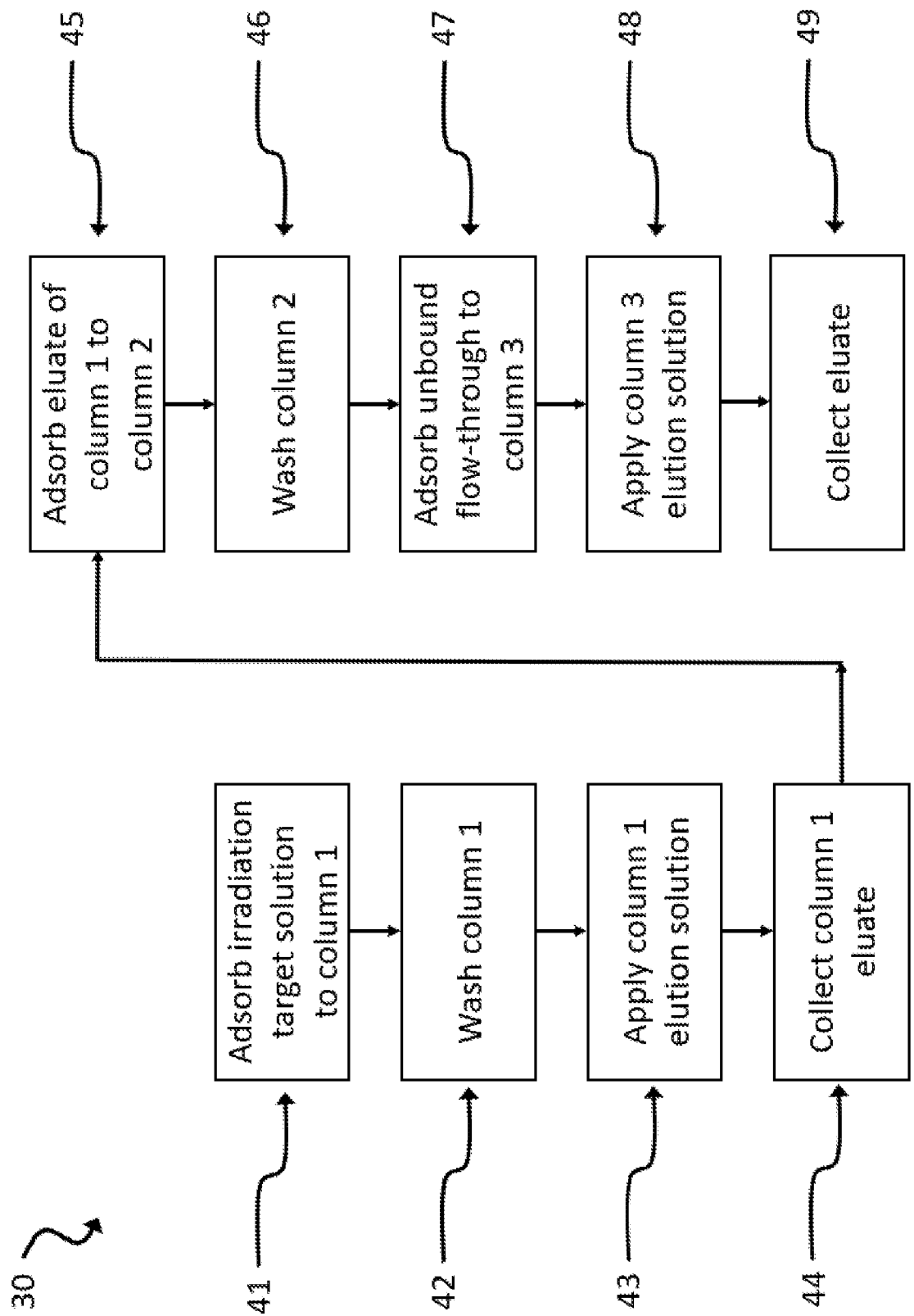
FIG. 3 shows a representative process of the present disclosure for the efficient and rapid isolation of Ga-68 produced using solid zinc targets irradiated by an accelerated particle beam.

Referring now to FIGS. 3A-3C, which disclose different detailed aspects and steps of the disclosed purification system 40. For example, FIG. 3A a disclosed purification system 40 wherein the desired eluate or flow-through material is discretely collected and then adsorbed a column or collected in the next step of the process. In a further aspect, FIG. 3B shows a disclosed purification system 40 wherein the desired eluate or flow-through material is directly adsorbed a column or collected in the next step of the process by valves that can direct waste or undesired materials away from the next column or step, and when needed the same valve can be adjusted or turned to direct the desired eluate or flow-through material to the next column or collected in a disclosed step. FIG. 3C shows a disclosed purification system 40 of FIG. 3C further comprising as a step the dissolution step 25. The various steps in FIGS. 3A-3C are labelled with reference numbers corresponding to those listed in the reference number glossary herein above.

Systems for Purification of Ga-68 from Irradiated Zn Target

In various aspects, the present disclosure pertains to systems that can be used to carry out the disclosed processes for purification of Ga-68 from a Zn target, wherein the disclosed systems comprise components and devices as disclosed herein. In a further aspect, the system can comprise a conveyance component, e.g., a liquid feed channel or tube, for conveying a sample to input component, such as a first inlet to which in turn is connected to a first controllable valve, that is connected to a first column. The first column can have directed to it through suitable conveyance components, e.g., feed channels or tube conveying a wash solution and/or a first elution solution from a first wash solution reservoir and a first elution reservoir, respectively. The first column has a first outlet that can be connected to a second controllable value which can direct fluid flow to a first waste stream or a first eluate stream connected to a second column. The unbound fluid flows through a second outlet of the second column, and the second outlet is connected to a third controllable valve, which is turn is connected to a third inlet of a third column. The third controllable value is also connected to a conveyance channel or tube that is connected to a second elution reservoir comprising a second elution solution. The third column has an outlet that is connected to a fourth controllable valve that can directed fluid flow to a second waste stream, i.e., comprising the flow-through of the third column comprising unbound material that entered the third column inlet, or to a second eluate stream comprising purified Ga-68.

It is understood that additional components can be utilized and that specific examples or aspects are not limited. For example, the system may contain additional tubing or channels between a valve and solution reservoir, column, inlet, and/or outlet to provide additional spacing between a valve and an outlet or inlet. Moreover, as used herein "channel" is intended to refer to a fluid conveyance channel as may be found in a microfluidic device. The disclosed columns, e.g., the first column, may further comprise elements of an integrated microfluidic device comprising the disclosed system to carry out the disclosed processes for purification of Ga-68 from a Zn target.

Figure 4:
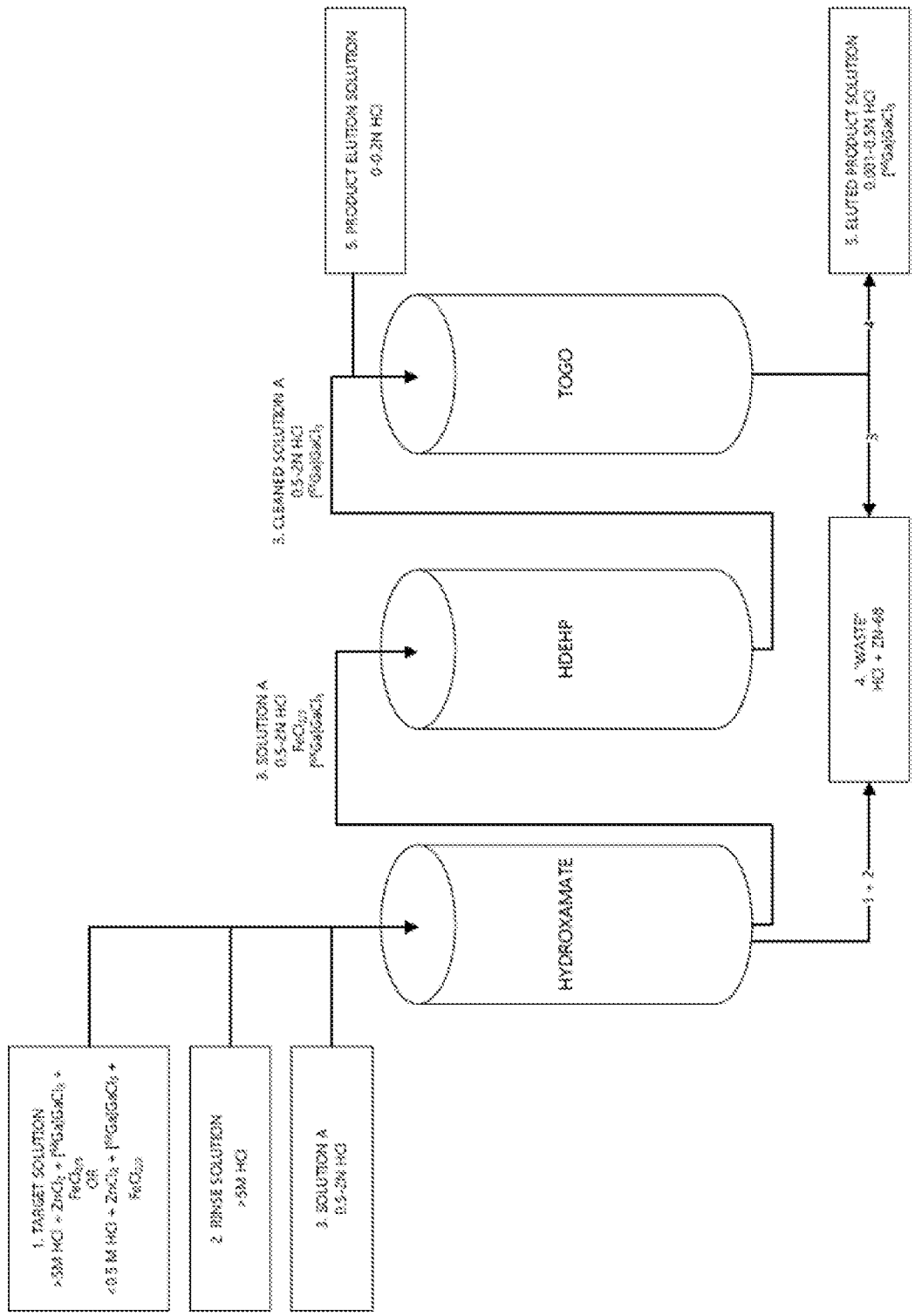
FIG. 4 shows a particular aspect of the disclosed processes and systems, e.g., as shown in FIG. 3.
Figure 5:
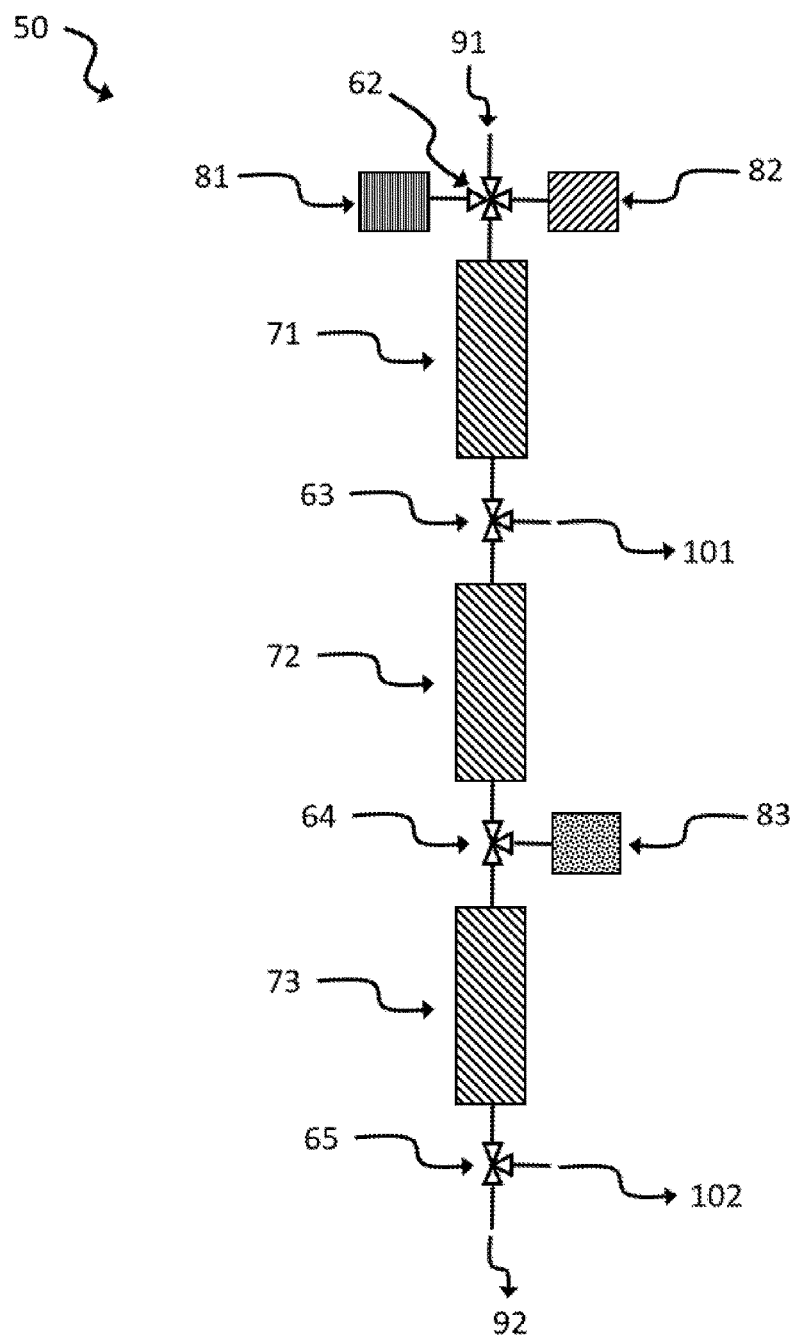
FIG. 5 shows a disclosed system for carrying out the disclosed process shown in FIG. 3B.

A representative disclosed system for carrying out the disclosed process shown in FIG. 3B is shown in FIG. 5. The various reference numbers in the process shown there refer to the reference numbers associated with various components and devices as listed in the reference number glossary herein above. In a specific aspect, a disclosed system is shown in FIG. 4.

From the foregoing, it will be understood that various aspects of the processes described herein are software processes that execute on computer systems that form parts of the system. Accordingly, it will be understood that various aspects of the system described herein are generally implemented as specially-configured computers including various computer hardware components and, in many cases, significant additional features as compared to conventional or known computers, processes, or the like, as discussed in greater detail herein. Aspects within the scope of the present disclosure also include computer-readable media for carrying or having computer-executable instructions or data structures stored thereon. Such computer-readable media can be any available media which can be accessed by a computer, or downloadable through communication networks. By way of example, and not limitation, such computer-readable media can comprise various forms of data storage devices or media such as RAM, ROM, flash memory, EEPROM, CD-ROM, DVD, or other optical disk storage, magnetic disk storage, solid state drives (SSDs) or other data storage devices, any type of removable non-volatile memories such as secure digital (SD), flash memory, memory stick, etc., or any other medium which can be used to carry or store computer program code in the form of computer-executable instructions or data structures and which can be accessed by a general purpose computer, special purpose computer, specially-configured computer, mobile device, etc.

When information is transferred or provided over a network or another communications connection (either hardwired, wireless, or a combination of hardwired or wireless) to a computer, the computer properly views the connection as a computer-readable medium. Thus, any such a connection is properly termed and considered a computer-readable medium. Combinations of the above should also be included within the scope of computer-readable media. Computer-executable instructions comprise, for example, instructions and data which cause a general purpose computer, special purpose computer, or special purpose processing device such as a mobile device processor to perform one specific function or a group of functions.

Those skilled in the art will understand the features and aspects of a suitable computing environment in which aspects of the disclosure may be implemented. Although not required, some of the aspects of the claimed disclosures may be described in the context of computer-executable instructions, such as program modules or engines, as described earlier, being executed by computers in networked environments. Such program modules are often reflected and illustrated by flow charts, sequence diagrams, exemplary screen displays, and other techniques used by those skilled in the art to communicate how to make and use such computer program modules. Generally, program modules include routines, programs, functions, objects, components, data structures, application programming interface (API) calls to other computers whether local or remote, etc. that perform particular tasks or implement particular defined data types, within the computer. Computer-executable instructions, associated data structures and/or schemas, and program modules represent examples of the program code for executing steps of the methods disclosed herein. The particular sequence of such executable instructions or associated data structures represent examples of corresponding acts for implementing the functions described in such steps.

Those skilled in the art will also appreciate that the claimed and/or described systems and methods may be practiced in network computing environments with many types of computer system configurations, including personal computers, smartphones, tablets, hand-held devices, multi-processor systems, microprocessor-based or programmable consumer electronics, networked PCs, minicomputers, mainframe computers, and the like. Aspects of the claimed disclosure are practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

An exemplary system for implementing various aspects of the described operations, which is not illustrated, includes a computing device including a processing unit, a system memory, and a system bus that couples various system components including the system memory to the processing unit. The computer will typically include one or more data storage devices for reading data from and writing data to. The data storage devices provide nonvolatile storage of computer-executable instructions, data structures, program modules, and other data for the computer.

Computer program code that implements the functionality described herein typically comprises one or more program modules that may be stored on a data storage device. This program code, as is known to those skilled in the art, usually includes an operating system, one or more application programs, other program modules, and program data. A user may enter commands and information into the computer through keyboard, touch screen, pointing device, a script containing computer program code written in a scripting language or other input devices (not shown), such as a microphone, etc. These and other input devices are often connected to the processing unit through known electrical, optical, or wireless connections.

The computer that effects many aspects of the described processes will typically operate in a networked environment using logical connections to one or more remote computers or data sources, which are described further below. Remote computers may be another personal computer, a server, a router, a network PC, a peer device or other common network node, and typically include many or all of the elements described above relative to the main computer system in which the disclosures are embodied. The logical connections between computers include a local area network (LAN), a wide area network (WAN), virtual networks (WAN or LAN), and wireless LANs (WLAN) that are presented here by way of example and not limitation. Such networking environments are commonplace in office-wide or enterprise-wide computer networks, intranets, and the Internet.

When used in a LAN or WLAN networking environment, a computer system implementing aspects of the disclosure is connected to the local network through a network interface or adapter. When used in a WAN or WLAN networking environment, the computer may include a modem, a wireless link, or other mechanisms for establishing communications over the wide area network, such as the Internet. In a networked environment, program modules depicted relative to the computer, or portions thereof, may be stored in a remote data storage device. It will be appreciated that the network connections described or shown are exemplary and other mechanisms of establishing communications over wide area networks or the Internet may be used.

While various aspects have been described in the context of a preferred aspect, additional aspects, features, and methodologies of the claimed disclosures will be readily discernible from the description herein, by those of ordinary skill in the art. Many aspects and adaptations of the disclosure and claimed disclosures other than those herein described, as well as many variations, modifications, and equivalent arrangements and methodologies, will be apparent from or reasonably suggested by the disclosure and the foregoing description thereof, without departing from the substance or scope of the claims. Furthermore, any sequence(s) and/or temporal order of steps of various processes described and claimed herein are those considered to be the best mode contemplated for carrying out the claimed disclosures. It should also be understood that, although steps of various processes may be shown and described as being in a preferred sequence or temporal order, the steps of any such processes are not limited to being carried out in any particular sequence or order, absent a specific indication of such to achieve a particular intended result. In most cases, the steps of such processes may be carried out in a variety of different sequences and orders, while still falling within the scope of the claimed disclosures. In addition, some steps may be carried out simultaneously, contemporaneously, or in synchronization with other steps.

The aspects were chosen and described in order to explain the principles of the claimed disclosures and their practical application so as to enable others skilled in the art to utilize the disclosures and various aspects and with various modifications as are suited to the particular use contemplated. Alternative aspects will become apparent to those skilled in the art to which the claimed disclosures pertain without departing from their spirit and scope. Accordingly, the scope of the claimed disclosures is defined by the appended claims rather than the foregoing description and the exemplary aspects described therein.

Radioimaging Compositions Comprising 68-Ga Prepared by the Disclosed Processes and Systems In various aspects, the present disclosure pertains to compositions comprising 68-Ga prepared using the disclosed processes and/or using the disclosed systems, e.g., radioimaging compositions comprising 68-Ga prepared using the disclosed processes and/or using the disclosed systems and a chelating agent for 68-Ga or radioimaging compositions comprising 68-Ga prepared using the disclosed processes and/or using the disclosed systems and an antibody such as, but not limited to, a monoclonal antibody.

In a further aspect, the radioimaging composition comprises 68-Ga prepared using the disclosed processes and/or using the disclosed systems and a chelating agent useful for clinical imaging. For example, suitable chelating agents include, but are not limited to, diethylenetriamine pentaacetic acid (DTPA), 1,4,7,10-tetraazacyclododecane N, N', N'', N''' tetraacetic acid (DOTA), [1,4,7-triazacyclononane-N,N',N''-triacetic acid] (NOTA), ethylenediamine tetraacetic acid (EDTA), N,N'-bis-[2-hydroxy-5-(carboxyethyl)benzyl] ethylenediamine-N,N'-diaceticacid (HBED-CC), and other known chelators can be used in accordance with the present invention. 68-Ga is readily chelated by such chelating agents. In a still further aspect, the chelate complex comprises 68-Ga prepared using the disclosed processes and/or using the disclosed systems and a di-DTPA derivative such as Ac-Phe-Lys(DTPA)-Tyr-Lys(DTPA)-$NH_2$.

In a further aspect, the radioimaging composition comprises 68-Ga prepared using the disclosed processes and/or using the disclosed systems and an antibody, e.g., a monoclonal antibody, a polyclonal antibody, an antibody fragement, and other suitable antibody derivatives.

The term "monovalent antibody fragment" as used herein denotes Fab' and Fab fragments, normally obtained by cleavage of bivalent fragments or intact immunoglobulin.

Fab' antibody fragments are normally and conveniently made by reductive cleavage of F(ab')2 fragments, which themselves are normally made by pepsin digestion of intact immunoglobulin. Fab antibody fragments can be made by papain digestion of intact immunoglobulin, under reducing conditions, or by cleavage of F(ab)2 fragments which result from careful papain digestion of whole 1 g. Parham et al., J. Immunol. Methods, 53:133-173, 1982, and Boguslawski et al., J. Immunol. Methods, 120:51-56, 1989, show papain digestion of murine monoclonal IgG1 to F(ab)2. Activation of the papain with thiol, followed by removal of the thiol prior to cleavage, permits cleavage of those immunoglobulins having the papain cleavage site below at least one disulfide bond to occur without further cleavage of the bivalent fragment.

It will be appreciated, however, that monovalent fragments can also include any fragments retaining the hypervariable, antigen-binding region of an immunoglobulin and having a size similar to or smaller than a Fab' fragment. This will include genetically engineered and/or recombinant proteins, whether single-chain or multiple-chain, which incorporate an antigen binding site and otherwise function in vivo as targeting vehicles in substantially the same way as natural monovalent immunoglobulin fragments.

It will also be understood that the monovalent antibody fragments to be radiolabeled can be fragments which bind to antigens which include but are not limited to antigens produced by or associated with tumors, infectious lesions, microorganisms, parasites, myocardial infarctions, atherosclerotic plaque, or normal organs or tissues.

The antibody fragment-chelate conjugates of the present invention can be prepared by known methods and the methods in, e.g., U.S. Pat. Nos. 5,612,016; 5,637,288; 5,635,603; and U.S. patent application Ser. Nos. 08/456,629; 08/779,556; and 08/456,909. Antibody fragments can be adapted for conjugation to a radioisotope, i.e., Ga-68, for use as a diagnostic imaging agent, herein, for positron emission tomography. This can be achieved by attaching a chelator for a radiometal or paramagnetic ion, according to the present invention, a compound that chelates Ga-68. Such chelators and their modes of attachment to antibodies are well known to the ordinary skilled artisan and are disclosed inter alia in, e.g., Childs et al., J. Nuc. Med., 26:293 (1985); and in Goldenberg U.S. Pat. Nos. 4,331,647, 4,348,376, 4,361,544, 4,468,457, 4,444,744, and 4,624,846. Typical are derivatives of ethylenediamine-tetraacetic acid (EDTA) and diethylenetriaminepentaacetic acid (DPTA). For example, Ac-Phe-Lys(DTPA)-Tyr-Lys(DTPA)-NH2 (SEQ ID NO:1) chelates Ga-68 and can be conjugated to an antibody fragment. These typically have groups on the side chain by which the chelator can be attached to an antibody fragment.

Alternatively, carboxyl or amine groups on a chelator can be activated and then coupled to an antibody fragment by well known methods.

The chelator may be bound to the antibody fragment, directly or through a short or long chain linker moiety, through one or more functional groups on the antibody, e.g., amine, carboxyl, phenyl, thiol or hydroxyl groups. Various conventional linkers can be used, e.g., diisocyanates, diisothiocyanates, carbodiimides, bis-hydroxysuccinimide esters, maleimide-hydroxysuccinimide esters, glutaraldehyde and the like, preferably a selective sequential linker such as the anhydride-isothiocyanate linker disclosed in U.S. Pat. No. 4,680,338.

In accordance with one embodiment, the bi-specific antibody comprises monoclonal antibodies or antibody fragments. In accordance with another embodiment, the bi-specific antibody comprises humanized antibodies or antibody fragments. Monoclonal antibodies (MAb) are usually mouse proteins, and they are not identical to human antibodies. Hence, antibodies from a mouse, when injected into a patient, will eventually be cleared from circulation as being recognized as foreign proteins. Both chains of the antibody molecule can be divided into variable and constant regions. In each antibody, the variable regions differ from one antibody to the next. This is the region that binds the antigen. The constant region of the antibody is the same among antibodies of the same type. The basic structure of a mouse Mab resembles that of a human antibody. However, there are numerous differences between amino acid sequences of the antibodies from the two species. These sequence differences account for the immunogenicity of mouse MAbs in humans. A chimeric Mab is constructed by ligating the cDNA fragment encoding the mouse light variable and heavy variable domains to fragment encoding the C domains from a human antibody. Because the C domains do not contribute to antigen binding, the chimeric antibody will retain the same antigen specificity as the original mouse Mab but will be closer to human antibodies in sequence. Chimeric Mabs still contain some mouse sequences, however, and may still be immunogenic. A humanized Mab contains only those mouse amino acids necessary to recognize the antigen. This product is constructed by building into a human antibody framework the amino acids from the mouse complementarity determining regions.

Multispecific, including bispecific and hybrid, antibodies and antibody fragments also may be used for detecting lesions and are comprised of at least two different substantially monospecific antibodies or antibody fragments, wherein at least two of said antibodies or antibody fragments specifically bind to at least two different antigens produced or associated with the targeted lesion or at least two different epitopes or molecules of a marker substance produced or associated with the targeted lesion. Multispecific antibodies and antibody fragments with dual specificities can be prepared analogously to the anti-tumor marker hybrids disclosed in U.S. Pat. No. 4,361,544. Other techniques for preparing hybrid antibodies are disclosed in, e.g., U.S. Pat. Nos. 4,474,893 and 4,479,895, and in Milstein et al., Immunol. Today, 5,299 (1984). These antibodies then are linked to an antibody or antibody fragment with chelate specificity to form the targeting antibody.

The antibodies against tumor antigens and against pathogens are known. For example, antibodies and antibody fragments which specifically bind markers produced by or associated with tumors or infectious lesions, including viral, bacterial, fungal and parasitic infections, and antigens and products associated with such microorganisms have been disclosed, inter alia, in Hansen et al., U.S. Pat. No. 3,927,193 and Goldenberg U.S. Pat. Nos. 4,331,647, 4,348,376, 4,361, 544, 4,468,457, 4,444,744, 4,818,709 and 4,624,846. In particular, antibodies against an antigen, e.g., a gastrointestinal, lung, breast, prostate, ovarian, testicular, brain or lymphatic tumor, a sarcoma or a melanoma, are advantageously used.

A wide variety of monoclonal antibodies against infectious disease agents have been developed, and are summarized in a review by Polin, in Eur. J. Clin. Microbiol., 3(5):387-398, 1984, showing ready availability.

Additional examples of Mabs generated against infectious organisms that have been described in the literature are noted.

Aspects

The following listing of exemplary aspects supports and is supported by the disclosure provided herein.

Aspect 1. A process for preparation of a carrier-free Ga-68 solution from a solid target assembly, the process comprising: adsorbing an irradiation target solution to a first chromatography column comprising a first chromatographic resin; washing the first chromatography column with a first chromatography wash solution; eluting a first eluate solution from the first chromatography column with a first chromatography column elution solution; adsorbing the first eluate solution to a second chromatography column comprising a second chromatography resin; collecting a second chromatography column flow-through solution from the second chromatography column; adsorbing the second chromatography column flow-through solution to a third chromatography column comprising a third chromatography resin; and eluting the carrier-free Ga-68 solution from the third chromatography column with a third chromatography column elution solution; wherein the irradiation target solution comprises a solution formed by dissolution of at least a portion of an irradiation target portion of a solid target assembly; wherein the irradiation target solution comprises Zn-68, Ga-68, and solid target assembly metals; wherein the solid target assembly comprises a metal disc comprising front and rear surfaces, and the irradiation target portion disposed on the top surface of the disc; wherein the irradiation target portion comprises a mixture of Zn-68 and Ga-68; wherein the first chromatography resin comprises a hydroxamate chromatography resin; wherein the first chromatography column wash solution has a strong acid present at a concentration of greater than about 4.5 M; wherein the first chromatography column elution solution has a strong acid present at a concentration of less than about 3.5 M; wherein the second chromatography resin comprises an alkyl phosphine oxide chromatography resin; wherein the third chromatography resin comprises an alkyl orthophosphoric acid chromatography resin; and wherein the third chromatography column elution solution is optionally comprises a strong acid present at a concentration less than about 0.2 M.

Aspect 2. The process of 1, wherein the irradiation target solution has a pH of from about 0.7 to about 4.

Aspect 3. The process of 1, wherein the irradiation target solution comprises a strong acid.

Aspect 4. The process of Aspect 3, wherein the strong acid is substantially free of trace metals.

Aspect 5. The process of Aspect 3, wherein the strong acid is HCl, $HNO_3$, or combinations thereof.

Aspect 6. The process of Aspect 3, wherein the strong acid is HCl; and wherein the HCl is present at a concentration of from about 4.5 M to about 12.2 M.

Aspect 7. The process of Aspect 6, wherein the strong acid is HCl; and wherein the HCl is present at a concentration of from about 8 M to about 12.2 M.

Aspect 8. The process of Aspect 7, wherein the strong acid is HCl; and wherein the HCl is present at a concentration of from about 12 M to about 12.2 M.

Aspect 9. The process of any one of Aspects 1-Aspect 6, wherein the solid target assembly metals comprise an aluminum salt, an iron salt, or combinations thereof.

Aspect 10. The process of any one of Aspects 1-Aspect 9, wherein the first chromatography resin has a capacity of from about 10 mg Zr per gram first chromatography resin to about 70 mg Zr per gram first chromatography resin when adsorbed in the presence of 2 M HCl.

Aspect 11. The process of any one of Aspects 1-Aspect 10, wherein the first chromatography column wash solution has a pH of from about 0.7 to about 4.0.

Aspect 12. The process of any one of Aspects 1-Aspect 11, wherein the first chromatography column wash solution is substantially free of trace metals.

Aspect 13. The process of any one of Aspects 1-Aspect 12, wherein the first chromatography column wash solution comprises HCl.

Aspect 14. The process of Aspect 13, wherein the HCl is present at a concentration of from about 4.5 M to about 12.2 M.

Aspect 15. The process of Aspect 14, wherein the HCl is present at a concentration of from about 8 M to about 12.2 M.

Aspect 16. The process of Aspect 15, wherein the HCl is present at a concentration of from about 12 M to about 12.2 M.

Aspect 17. The process of any one of Aspects 1-Aspect 16, wherein the first chromatography column elution solution comprises HCl.

Aspect 18. The process of Aspect 17, wherein the HCl is present at a concentration of from about 0.2 M to about 3.5 M.

Aspect 19. The process of Aspect 18, wherein the HCl is present at a concentration of from about 0.5 M to about 3 M.

Aspect 20. The process of Aspect 19, wherein the HCl is present at a concentration of from about 1 M to about 2 M.

Aspect 21. The process of any one of Aspects 1-Aspect 20, wherein the third chromatography column elution solution does not comprise a strong acid.

Aspect 22. The process of Aspect 21, wherein the third chromatography column elution solution consists essentially of water.

Aspect 23. The process of Aspect 21, wherein the third chromatography column elution solution is substantially free of trace metals.

Aspect 24. The process of any one of Aspects 1-Aspect 23, wherein the third chromatography column elution solution comprises HCl.

Aspect 25. The process of Aspect 24, wherein the third chromatography column elution solution is substantially free of trace metals.

Aspect 26. The process of Aspect 24, wherein the HCl is present at a concentration of from about 0.01 M to about 0.2 M.

Aspect 27. The process of Aspect 26, wherein the HCl is present at a concentration of from about 0.01 M to about 0.1 M.

Aspect 28. The process of Aspect 27, wherein the HCl is present at a concentration of from about 0.01 M to about 0.05 M.

Aspect 29. The process of any one of Aspects 1-Aspect 28, wherein the carrier-free Ga-68 solution has a radionuclide purity of greater than about 98%; and wherein the radionuclide purity is defined as the ratio of 68Ga to the aggregate of 66 Ga and 67Ga and 68Ga.

Aspect 30. The process of Aspect 29, wherein the carrier-free Ga-68 solution has a radionuclide purity of greater than about 99%.

Aspect 31. The process of Aspect 29, wherein the carrier-free Ga-68 solution has a radionuclide purity of greater than about 99.5%.

Aspect 32. The process of Aspect 29, wherein the carrier-free Ga-68 solution has a radionuclide purity of greater than about 99.7%.

Aspect 33. The process of any one of Aspects 1-Aspect 32, wherein the carrier-free Ga-68 solution has iron present in an amount less than about 10 μg per GBq Ga-68.

Aspect 34. The process of Aspect 33, wherein the iron is present in an amount less than about 5 μg per GBq Ga-68.

Aspect 35. The process of Aspect 33, wherein the iron is present in an amount less than about 1 μg per GBq Ga-68.

Aspect 36. The process of Aspect 33, wherein the iron is present in an amount less than about 0.1 μg per GBq Ga-68.

Aspect 37. The process of any one of Aspects 1-Aspect 36, wherein the carrier-free Ga-68 solution has Zn present in an amount less than about 10 μg per GBq Ga-68.

Aspect 38. The process of Aspect 37, wherein the zinc is present in an amount less than about 5 μg per GBq Ga-68.

Aspect 39. The process of Aspect 37, wherein the zinc is present in an amount less than about 1 μg per GBq Ga-68.

Aspect 40. The process of Aspect 37, wherein the zinc is present in an amount less than about 0.5 μg per GBq Ga-68.

Aspect 41. The process of any one of Aspects 1-Aspect 36, wherein the carrier-free Ga-68 solution is substantially free of other radionuclides.

Aspect 42. A Ga-68 composition comprising Ga-68 obtained from the carrier-free Ga-68 solution prepared by the process of any one of Aspects 1-Aspect 41.

Aspect 43. An imaging reagent comprising Ga-68 composition of Aspect 42.

Aspect 44. The imaging reagent of Aspect 43, wherein the imaging reagent $^{68}$Ga-PSMA-617, $^{68}$Ga-PSMA-11, $^{68}$Ga-DOTATATE, $^{68}$Ga-DOTATOC, $^{68}$Ga-DOTANOC, or combinations thereof.

From the foregoing, it will be seen that aspects herein are well adapted to attain all the ends and objects hereinabove set forth together with other advantages which are obvious and which are inherent to the structure.

While specific elements and steps are discussed in connection to one another, it is understood that any element and/or steps provided herein is contemplated as being combinable with any other elements and/or steps regardless of explicit provision of the same while still being within the scope provided herein.

It will be understood that certain features and subcombinations are of utility and may be employed without reference to other features and subcombinations. This is contemplated by and is within the scope of the claims.

Since many possible aspects may be made without departing from the scope thereof, it is to be understood that all matter herein set forth or shown in the accompanying drawings and detailed description is to be interpreted as illustrative and not in a limiting sense.

It is also to be understood that the terminology used herein is for the purpose of describing particular aspects only and is not intended to be limiting. The skilled artisan will recognize many variants and adaptations of the aspects described herein. These variants and adaptations are intended to be included in the teachings of this disclosure and to be encompassed by the claims herein.

Now having described the aspects of the present disclosure, in general, the following Examples describe some additional aspects of the present disclosure. While aspects of the present disclosure are described in connection with the following examples and the corresponding text and figures, there is no intent to limit aspects of the present disclosure to this description. On the contrary, the intent is to cover all alternatives, modifications, and equivalents included within the spirit and scope of the present disclosure.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the disclosure and are not intended to limit the scope of what the inventors regard as their disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1

Irradiation of Zn Target

The target used in these studies comprised Zn-68 filled in a 10 mm diameter recess on a silver backing and were irradiated using an ARTMS solid target system installed on a GE PETtrace cyclotrons. A GE energy degrader was used to drop the proton energy down to 13 MeV, the energy was confirmed by irradiation of copper foils. Various target parameters and irradiation conditions were assessed for optimal production of Ga-68 as described in Table 1, i.e., up to 80 uA, and bombarded for up to 2 hours. Specific irradiation trials are shown in Table 2. The data below show that a yield up to 194 GBq (5.2 Ci) [$^{68}$Ga]GaCl$_3$ could be obtained. Based on the decay corrected recovery yield of gallium-68 using the disclosed methods, it was calculated that over 10 Ci [$^{68}$Ga]GaCl$_3$ was produced at time end of bombardment.

TABLE 1

| Parameter | Value |
| --- | --- |
| $^{68}$Zn Loading | 230-320 mg |
| $^{68}$Zn coated diameter | 10 mm |
| Bombardment Energy | 13.0 MeV |
| Beam Current | up to 80 μA |
| Bombardment Time | up to 2 hours |
| Angle to Beam | 90° |
| Backing material | Silver |

TABLE 2

| Parameter | 1 | 2 | 3 | 4 | 5 |
| --- | --- | --- | --- | --- | --- |
| Beam Current | 10 μA | 50 μA | 70 μA | 80 μA | 80 μA |
| Bombardment time | 5 min | 30 min | 30 min | 120 min | 120 min |
| Target Loading | 270 mg | 315 mg | 230 mg | 240 mg | 300 mg |
| [$^{68}$Ga]GaCl$_3$ Isolated | 0.90 GBq | 35 GBq | 45 GBq | 152 GBq | 194 GBq |

Example 2

Exemplary Purification of 68-Ga Using a Disclosed Process

Figure 6C:
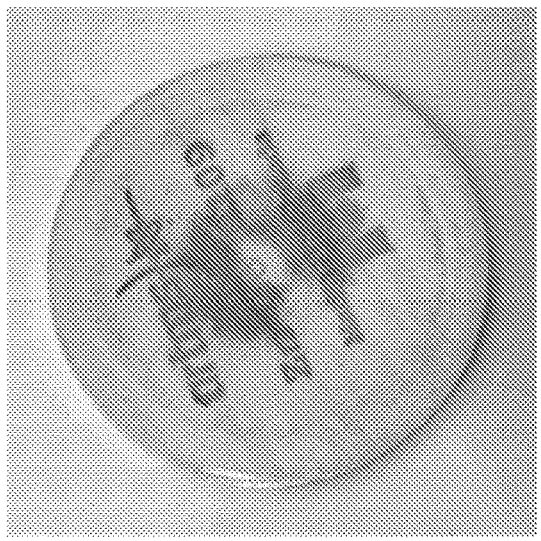
FIGS. 6A-6C show representative photographic images of targets.
Figure 6B:
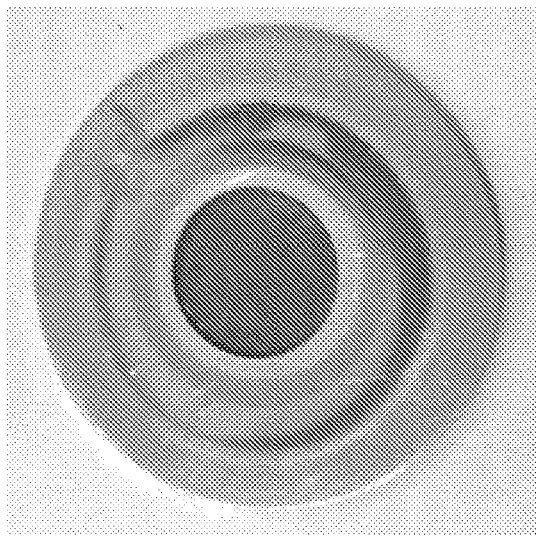
Figure 6A:
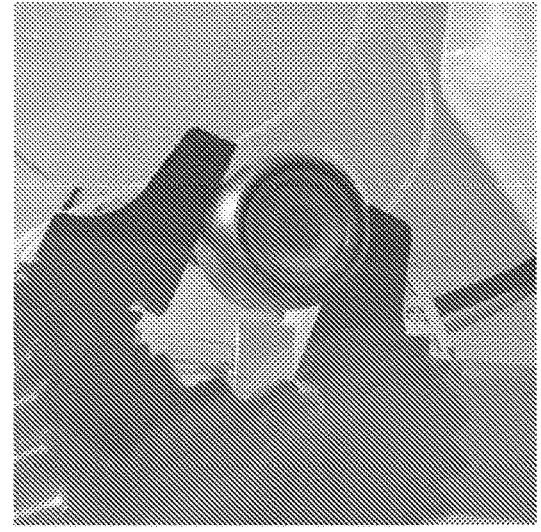

Using the foregoing methods, an irradiated target comprising 300 mg Zn-68/Ga-68 and other metals was dissolved 2 mL 9.5 N HCl to provide a target irradiation solution. Data for recovery of Ga-68 in the dissolution step are shown in Table 2 below. Exemplary photographic images of an irradiated target, a target following the foregoing dissolution step, and the reverse side of an irradiated target are shown in FIGS. 6A-6C, respectively.

TABLE 3

| Dissolution | 9.5N HCl (2 mL) |
|---|---|
| Temperature | 100° C. |
| Dissolution time | 11 min |
| Amount $^{68}$Zn Dissolved | >98% (n > 10) |

The target irradiation solution was adsorbed onto the first chromatography column, and then the column was washed with 15 mL 9.5 N HCl. The first chromatography column was eluted using 8 mL 1.0 N HCl, and the eluate was flowed directly onto the second chromatography column, and the flow through from the second chromatography column was adsorbed onto the third chromatography column. The third chromatography colum was eluted with using 3 mL 0.1 N HCl. The first chromatography resin was a hydroxyamate resin, i.e., 250 mg ZR resin (Triskem International, Bruz, France); the second chromatography resin was a di(2-ethylexyl)orthophosphoric acid ("HDEHP") resin, i.e., 500 mg LN resin (Triskem International); and the third chromatography resin was a trioctylphosphine oxide ("TOPO") resin, i.e., 200 mg TK200 200 mg TK200 resin (Triskem International). The foregoing separation steps were carried with an approximate processing time of 22 minutes; and the total process time, i.e., from the end of proton irradiation to isolated purified carrier-free gallium chloride in solution, was about 37 minutes. The quality control assessment based on four batches of the purified Ga-68 sample obtained in this example is shown below in Table 4 and compared to the specifications set forth in "Gallium (68Ga) Chloride (Accelerator-Produced) Solution for Radiolabelling" (Ph. Eur. Monograph draft 3109). The radionuclide purity obtained allowed for a shelf-life of up to about 7 hours. Moreover, the data indicate a low amount of metallic impurities in the produced gallium-68, i.e., similar to what is observed for the generator-produced isotope.

TABLE 4

| Parameter | Monograph‡ | Result (n = 4) |
|---|---|---|
| Processing Time | No spec | ≤37 min from EOB |
| pH | <2 | <2 |
| Fe content | <10 µg/GBq | 0.015 ± 0.014 µg/GBq |
| Zn content | <10 µg/GBq | 0.40 ± 0.35 µg/GBq |
| Bacterial Endotoxins | <175 IU/V | <2 IU/mL |
| Radionuclidic Purity $^{68}$Ga/($^{66/67/68}$Ga) | >98% | 99.92 ± .05% |

TABLE 4-continued

| Parameter | Monograph‡ | Result (n = 4) |
|---|---|---|
| Other radionuclides | <0.1% | Not detected |
| TLC* | >95% $Ga^{3+}$ | >99.9% $Ga^{3+}$ |
| Radiolabeling | No spec | >23 MBq/nmol DOTATATE/PSMA-11 |

‡Gallium (68 Ga) Chloride (Accelerator-Produced) Solution for Radiolabelling, Ph. Eur. Monograph draft 3109.
*Purity as determined by thin layer chromatography.

Example 3

Assessment of Iron Removal in Disclosed Process

Further studies were carried out to assess the efficiency of iron removal in a disclosed process by spiking iron into a composition comprising a solution of similar composition to a solution obtained from a dissolved target, but absent 68-Ga. Briefly, the study was carried out as follows: 1) dissolved natural Zinc Target using the dissolution method described herein above; 2) Stopped the process described above to collect a small sample of the dissolve natural zinc in a reactor vial) the amount of natural zinc recovered is shown below in Table 5); 3) Spiked the reactor vial with Fe prepped from FeSO4.7H2O (in the amount shown below in Table 5); 4) Mix and collected a small sample of dissolved Natural Zinc with Fe spike; 5) continue the process for purification as described above to completion; 6) Collect a small sample of Waste vial solution (waste collected from column 3 following wash step); 7) Collect a small sample of Product vial solution (sample eluated from column 3 following elution step); and 8) Analyzed four collected solutions by ICPOES and ICPMS as shown below. The data show that the greater than 98.6% of the original spiked iron was removed. However, if the total amount of iron present, inclusive of the amount likely present in the zinc target sample itself, then greater than 99.7 wt % of the iron present in the dissolved sample was removed. The overall procedure for Inductively Coupled Plasma Analysis as used herein in described following Table 5.

TABLE 5

| Sample Description | Zn (mg) | Fe (µg) |
|---|---|---|
| Un-spiked sample | 253.20 | Not applicable |
| Spiked sample | 250.04 | 21.86 |
| Waste vial | 73.75 | 114.30* |
| Product vial | 0.03 | 0.32 |

*The apparent amount observed is likely due to the presence of Fe in the Zn used in the target material.

Samples for Inductively Coupled Plasma Analysis were prepared as follows: 1) Sample aliquots taken during the running of the Trasis Mini-AiO Synthesis were evaporated to incipient dryness; 2) Samples were reconstituted in HNO3 (2M) to a known volume. Depending on the estimated concentration of Zn in the stock solutions, the samples were appropriately diluted in HNO3 (2% v/v) to an approximate Zn concentration of 100 ppm in order to ensure that the sample did not contaminate inductively coupled plasma mass spectrometry instrumentation or result in significant isobaric and polyatomic interferences or induce memory effects); 3) If the expected concentration of Zn was 0, i.e. the product vial, the sample was evaporated to incipient dryness and reconstituted to a known volume in HNO3 (2% v/v) for analysis; 4) Final sample volumes for all samples was 10 mL for ICP-MS analysis of trace elements; 5) Samples were transferred to a 15 mL Falcon tube and spiked with an indium internal standard solution (100 µL, 1 ppm); 6) further 10× dilution of ICP-MS samples was completed for the analysis of Fe and Zn by ICP-OES using HNO3 (2% v/v); and 7)Final sample volumes for ICP-OES analysis was 5 mL.

Standard samples for Inductively Coupled Plasma Analysis were prepared as follows: 1) Mixed analyte calibration standard (containing 52 elements in total) were prepared in the range of 0-50 ppb for ICP-MS analysis in a HNO3 (2% v/v) matrix. (Note: Zn was not analysis for by ICP-MS as the high concentrations present would damage the instrument detector); 2) ICP-MS standards were spiked with 10 ppm indium as an internal standard; and 3) Mixed calibration standards containing Fe and Zn were prepared in the range of 0-10 ppm for ICP-OES analysis in a HNO3 (2% v/v) matrix.

Blank samples preparation and limit of detection calibration: 1) 6 $HNO_3$ (2% v/v) blank samples were spiked with 10 ppm indium as an internal standard; 2) Limit of detection was calculated as:

$LOD = 3 \times \text{Standard Deviation}_{(Blanks)}$;

3) Limit of quantification was calculated as:

$LOQ = 10 \times LOD$;

4) It was assumed that the associated error of results greater that the LOD was ±20% where as the associated error of result between the LOD and LOQ is significantly greater; and 5) The same method of detection limit calculation was applied to both ICP-MS and ICP-OES analysis.

Method of analysis was as follows: 1) Trace elemental analysis of 52 elements (including Fe) was completed using quadrupole ICP-MS; and 2) The analysis of Fe and Zn was completed using ICP-OES.

Example 4

Radioimaging Compositions Comprising 68-Ga

Purified 68-Ga were used to preparing radioimaging compositions as shown below in Table 6. The data shown in Table 6 and other studies suggest that radiolabeling of DOTATATE and PSMA-HBED-11 were performed in high yields (>95%) and in clinically acceptable molar specific radioactivity (≥24 MBq/nmol, non-optimized).

TABLE 5

| Parameter | PSMA-11 (n = 1) | DOTATATE (n = 1) |
| --- | --- | --- |
| Isolated Product | 39 GBq (1.2 Ci) | 11 GBq (300 mCi) |
| RCP | 99.9% | *84.5% |
| Specific Activity | 370 MBq $^{68}$Ga/nmol PSMA-11 | *134 MBq $^{68}$Ga/nmol DOTATATE |

*Suspected radiolysis and not chemical impurities.

It should be emphasized that the above-described aspects of the present disclosure are merely possible examples of implementations set forth for a clear understanding of the principles of the disclosure. Many variations and modifications may be made to the above-described aspect(s) without departing substantially from the spirit and principles of the disclosure. All such modifications and variations are intended to be included herein within the scope of this disclosure and protected by the following claims.

What is claimed is:

1. A process for preparation of a carrier-free Ga-68 solution from a solid target assembly, the process comprising:
adsorbing an irradiation target solution to a first chromatography column comprising a first chromatographic resin;
washing the first chromatography column with a first chromatography wash solution;
eluting a first eluate solution from the first chromatography column with a first chromatography column elution solution;
adsorbing the first eluate solution to a second chromatography column comprising a second chromatography resin;
collecting a second chromatography column flow-through solution from the second chromatography column;
adsorbing the second chromatography column flow-through solution to a third chromatography column comprising a third chromatography resin; and
eluting the carrier-free Ga-68 solution from the third chromatography column with a third chromatography column elution solution;
wherein the irradiation target solution comprises a solution formed by dissolution of at least a portion of an irradiation target portion of a solid target assembly;
wherein the irradiation target solution comprises Zn-68, Ga-68, and solid target assembly metals;
wherein the solid target assembly comprises a metal disc comprising front and rear surfaces, and the irradiation target portion disposed on the top surface of the disc;
wherein the irradiation target portion comprises a mixture of Zn-68 and Ga-68;
wherein the first chromatography resin comprises a hydroxamate chromatography resin;
wherein the first chromatography column wash solution has a strong acid present at a concentration of greater than about 4.5 M;
wherein the first chromatography column elution solution has a strong acid present at a concentration of less than about 3.5 M;
wherein the second chromatography resin comprises an alkyl orthophosphoric acid chromatography resin;
wherein the third chromatography resin comprises an alkyl phosphine oxide resin chromatography resin; and
wherein the third chromatography column elution solution optionally comprises a strong acid present at a concentration less than about 0.2 M.

2. The process of claim 1, wherein the irradiation target solution comprises a strong acid.

3. The process of claim 2, wherein the strong acid is substantially free of trace metals; and wherein the strong acid is selected from HCl, HNO3, and combinations thereof.

4. The process of claim 3, wherein the strong acid is HCl; and wherein the HCl is present at a concentration of from about 12 M to about 12.2 M.

5. The process of claim 1, wherein the solid target assembly metals comprise an aluminum salt, an iron salt, or combinations thereof.

6. The process of claim 1, wherein the first chromatography column wash solution has a pH of from about 0.7 to about 4.0.

7. The process of claim 1, wherein the first chromatography column wash solution is substantially free of trace metals.

8. The process of claim 1, wherein the first chromatography column wash solution comprises HCl.

9. The process of claim 1, wherein the first chromatography column elution solution comprises HCl.

10. The process of claim 9, wherein the HCl is present at a concentration of from about 1 M to about 2 M.

11. The process of claim 1, wherein the third chromatography column elution solution does not comprise a strong acid.

12. The process of claim 11, wherein the third chromatography column elution solution consists essentially of water; and wherein the third chromatography column elution solution is substantially free of trace metals.

13. The process of claim 1, wherein the third chromatography column elution solution comprises HCl; and wherein the third chromatography column elution solution is substantially free of trace metals.

14. The process of claim 13, wherein the HCl is present at a concentration of from about 0.01 M to about 0.05 M.

15. The process of claim 1, wherein the carrier-free Ga-68 solution has a radionuclide purity of greater than about 98%; and wherein the radionuclide purity is defined as the ratio of $^{68}$Ga to the aggregate of $^{66}$Ga and $^{67}$Ga and $^{68}$Ga.

16. The process of claim 15, wherein the carrier-free Ga-68 solution has a radionuclide purity of greater than about 99.7%.

17. The process of claim 1, wherein the carrier-free Ga-68 solution has iron present in an amount less than about 10 µg per GBq Ga-68.

18. The process of claim 17, wherein the iron is present in an amount less than about 0.1 µg per GBq Ga-68.

19. The process of claim 1, wherein the carrier-free Ga-68 solution has Zn present in an amount less than about 10 µg per GBq Ga-68.

20. The process of claim 19, wherein the zinc is present in an amount less than about 0.5 µg per GBq Ga-68.

21. The process of claim 1, wherein the carrier-free Ga-68 solution is substantially free of other radionuclides.

\* \* \* \* \*